United States Patent
Patel et al.

(10) Patent No.: US 7,423,004 B2
(45) Date of Patent: Sep. 9, 2008

(54) SOLID DISPERSION COMPOSITIONS

(75) Inventors: Kamlesh H. Patel, King of Prussia, PA (US); Raviraj S. Pillai, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 481 days.

(21) Appl. No.: 10/543,012

(22) PCT Filed: Jan. 30, 2004

(86) PCT No.: PCT/US2004/002833

§ 371 (c)(1),
(2), (4) Date: Jul. 22, 2005

(87) PCT Pub. No.: WO2004/069180

PCT Pub. Date: Aug. 19, 2004

(65) Prior Publication Data

US 2006/0052270 A1   Mar. 9, 2006

Related U.S. Application Data

(60) Provisional application No. 60/444,085, filed on Jan. 31, 2003.

(51) Int. Cl.
C11D 1/68 (2006.01)
C11D 3/20 (2006.01)
C11D 13/12 (2006.01)
A01N 25/28 (2006.01)
A61K 9/127 (2006.01)

(52) U.S. Cl. ............ 510/441; 510/438; 510/445; 424/417; 424/419; 424/450; 424/497; 424/498

(58) Field of Classification Search ............... 510/438, 510/441, 445; 424/417, 419, 450, 497, 498
See application file for complete search history.

(56) References Cited

U.S. PATENT DOCUMENTS

| 4,386,895 A | 6/1983 | Sodickson ............ 425/5 |
| 4,578,391 A | 3/1986 | Kawata et al. ........ 514/256 |
| 4,668,513 A | 5/1987 | Reichert ............. 424/94 |
| 4,675,140 A | 6/1987 | Sparks et al. ........ 264/4.3 |

(Continued)

FOREIGN PATENT DOCUMENTS

EP    0431659 B1    4/1994

(Continued)

OTHER PUBLICATIONS

Porter et al. *Advanced Drug Delivery Reviews*, 50: S127-S147 (2001). no month given.

(Continued)

*Primary Examiner*—Brian Mruk
(74) *Attorney, Agent, or Firm*—Kathryn L. Sieburth; Mary E. McCarthy; Charles M. Kinzig

(57) ABSTRACT

Disclosed is a water-dispersible solid composition of a sparingly water-soluble compound in a particulatable lipidic carrier, methods for the preparation and use of the same. The compositions of this intention provide improved solubility and dissolution characteristics and enhanced bioavailability of the sparingly soluble compound.

19 Claims, 6 Drawing Sheets

U.S. PATENT DOCUMENTS

| | | | |
|---|---|---|---|
| 4,801,460 A | 1/1989 | Goertz et al. | 424/465 |
| 4,880,585 A | 11/1989 | Klimesch et al. | 264/141 |
| 4,957,681 A | 9/1990 | Klimesch et al. | 264/211.23 |
| 5,028,432 A | 7/1991 | Chopra et al. | 414/451 |
| 5,051,261 A | 9/1991 | McGinity et al. | 424/464 |
| 5,073,379 A | 12/1991 | Klimesch et al. | 424/467 |
| 5,234,695 A | 8/1993 | Hobbs et al. | 424/489 |
| 5,292,657 A | 3/1994 | Rutherford et al. | 435/243 |
| 5,433,951 A | 7/1995 | Serajuddin et al. | 424/486 |
| 5,456,923 A | 10/1995 | Nakamichi et al. | 424/489 |
| 5,601,761 A | 2/1997 | Hoffman et al. | 264/4.3 |
| 5,665,369 A | 9/1997 | Wedlock et al. | 424/408 |
| 5,891,469 A | 4/1999 | Amselem | 424/451 |
| 5,939,099 A | 8/1999 | Grabowski et al. | 424/488 |
| 6,001,391 A | 12/1999 | Zeidler et al. | 424/467 |
| 6,051,253 A | 4/2000 | Zettler et al. | 424/465 |
| 6,120,802 A | 9/2000 | Breitenbach et al. | 424/464 |
| 6,248,363 B1 * | 6/2001 | Patel et al. | 424/497 |
| 6,316,473 B1 | 11/2001 | Shimojo et al. | 514/336 |
| 6,395,300 B1 | 5/2002 | Straub et al. | 424/489 |

FOREIGN PATENT DOCUMENTS

| | | |
|---|---|---|
| EP | 0901786 A2 | 3/1999 |
| EP | 1 027 886 | 8/2000 |
| EP | 1 027 887 | 8/2000 |
| EP | 1027885 A2 | 8/2000 |
| EP | 1027886 A2 | 8/2000 |
| EP | 0942743 B1 | 3/2002 |
| GB | 1090971 | 11/1967 |
| WO | WO 93/11749 A1 | 6/1993 |
| WO | WO 93/23022 | 11/1993 |
| WO | WO 96/22103 A1 | 7/1996 |
| WO | WO 97/02017 A1 | 1/1997 |
| WO | WO 97/35587 A1 | 10/1997 |
| WO | WO 98/08490 A1 | 3/1998 |
| WO | WO 98/10754 A1 | 3/1998 |
| WO | WO 01/74357 A2 | 10/2001 |
| WO | WO 01/95939 A1 | 12/2001 |

OTHER PUBLICATIONS

Wade Schlameus. Chapter 9: Centrifugal Extrusion Encapsulation. *ACS Symposium Series 590.* American Chemical Society, 1995. no month given.

* cited by examiner

SOLID DISPERSION COMPOSITIONS

This application is a 371 of International Application No. PCT/US2004/002833, filed 30 Jan. 2004.

This application claims benefit of Provisional Application No. 60/444,085, filed Jan. 31, 2003.

FIELD OF THE INVENTION

This invention relates to solid, water dispersible, particulate compositions consisting of molecular dispersions of compounds, specifically sparingly water-soluble compounds, and/or a pharmaceutical salt thereof, in a lipidic matrix. In particular, this invention is directed to solid molecular dispersions that provide improved solubility and dissolution, as well as enhanced bioavailability, of the compound dispersed therein. Also provided are methods for the preparation and use of these solid molecular dispersions.

BACKGROUND OF THE INVENTION

A solid dispersion is a molecular dispersion of a compound, particularly a drug substance, within a lipidic carrier matrix. Formation of a molecular dispersion (solid solutions) of such a compound provides a means of reducing the particle size of the compound to nearly molecular levels (i.e. there are no particles). As the carrier dissolves, the compound is exposed to the dissolution media as fine particles that are amorphous, which can dissolve and be absorbed more rapidly than larger particles. The use of solid dispersion compositions of sparingly soluble compounds has been used to enhance the solubility, dissolution and bioavailability of the sparingly water-soluble compound.

Conventional techniques for producing solid dispersions include melt processing, wherein the compound and a carrier are heated to a temperature above the melting point of both the carrier and compound, which results in the formation of a fine colloidal (as opposed to molecular) dispersion of compound particles, with some solubilization of the compound in the carrier matrix. Processing of such a molten mixture often includes rapid cooling, which results in the formation of a congealed mass which must be subsequently milled to produce a powder which can be filled into capsules or made into tablets. This melt processing technique has several disadvantages. For example, if the compound and carrier are not miscible in the molten state, non-homogeneous mixtures may be formed. In addition, the process is also limited for use with compounds and carriers that do not decompose at high temperatures required to melt the components.

When difficulty arises with thermal instability and/or miscibility between the compound and the carrier, a hybrid method for making solid dispersions, called the fusion-solvent method may be used. In this technique, the compound substance is first dissolved in a small quantity of organic solvent and then added to a molten carrier. The solvent is then evaporated to generate a product that can be subsequently milled to produce a powder. This solvent process also has disadvantages, for example, explosion hazard during production, difficulty in removing all traces of solvent from the solid dispersion product for pharmaceutical use, diffusion of solvent into the atmosphere causing pollution and the potential for compound recrystallization following solvent removal.

Stability of these conventional formulations can be problematic. The use of high heat or the use of organic solvents may be required to solubilize the compound into the carrier matrix. After removal of these solubilization factors (i.e., after cooling or removal of the solvent), the compound may no longer be soluble in the carrier. In the most problematic cases, recrystallization of the compound in the dispersion matrix may occur, leading to significant reduction in the dissolution and bioavailability of the compound.

Post-processing of these conventional formulations to prepare the final physical form of the compound ingredient may also be problematic. For example, some of the conventional dispersions described above, particularly those prepared using organic solvents, must be processed by milling to obtain the fine particles required for final product (e.g., tabletting or capsule filling). Milling or similar size reduction processes, however, provides irregularly shaped particles that are polydisperse, which may contribute to variability in dissolution rates. Conventional formulations that require processing at highly elevated temperatures may also require extended cooling times. In addition, other special processing may be required when handling these formulations to minimize recrystallization of the compound within the carrier matrix. Problems may also arise during the dissolution of compound from dosage forms prepared using such conventional formulation technology. Generally, the carriers used to prepare the solid dispersions, such as high molecular weight (MW>3000) polyethylene glycols (PEGs), polyvinylpyrrolidone (PVP), hydroxypropylmethylcellulose (HPMC), and the like, possess better water solubility characteristics than the compounds dispersed therein. As the carriers preferentially dissolve, tiny amounts of the slowly dissolving compound are left on the surface of the solid particles. If the rate of dissolution of the carrier is much greater than the rate of compound dissolution, agglomeration or crystallization of the compound may occur, thereby reducing its dissolution in the gastrointestinal (GI) media which may result in reduced bioavailability. In addition, these carriers does not have the ability to emulsify precipitated particles which can also adversely affect the dissolution and bioavailability of the compound.

Accordingly, it would be desirable to provide a formulation for compounds, particularly sparingly soluble compounds, that would provide enhanced bioavailability characteristics, that can be processed into a variety of final physical forms, and that can be prepared using mild formulation conditions, without the need for using organic solvents and without the need to heat the compound to temperatures above its melting point.

SUMMARY OF THE INVENTION

Figure 1:
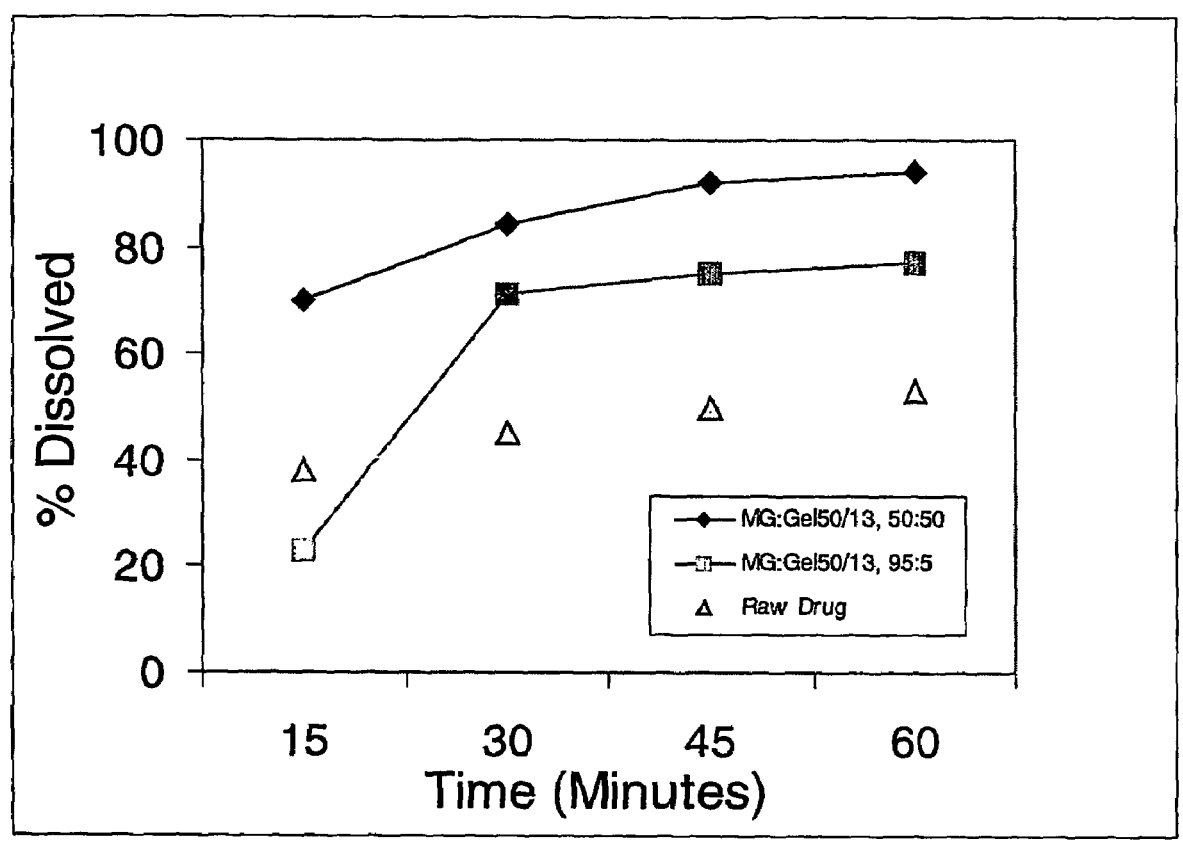
FIG. 1 illustrates the rate of dissolution of a unit dose of a compound, alone, and as formulated in two water-dispersible lipidic carriers, composed of glycerol monostearate and Gelucire®50/13 at weight ratios of 50:50 and 90:5.

This invention is directed to water-dispersible, particulate pharmaceutical compositions, methods for their preparation and their use, in dosage form, comprising a solid, molecularly dispersed solution of about 0.01% to about 15% by weight of a sparingly water-soluble compound, and about 85-99.99% by weight of a particulatable lipid-based carrier, wherein the compound has a solubility in water of less than 100 µg/mL at 25° C. and the particulatable lipid-based carrier is comprised of about 5% to about 50% by weight of a lipid-based surfactant selected from the group consisting of polyglycolized glycerides, a polyoxyethylene castor oil derivative, a polyoxyethylene stearate, and a mixture thereof, and about 50% to about 95% by weight of a stiffening agent having a melting point from 50° C. to 80° C. comprising mono-, di- or triglycerides, or a mixture thereof, and selected from the group consisting of glycerol monostearate, glycerol palmitostearate, hydrogenated vegetable oil, and a mixture thereof.

More specifically, this invention relates to a solid molecular dispersion wherein a sparingly water-soluble compound is dissolved in a particulatable lipidic carrier, without the use of organic solvents and without heating the compound to its melting temperature (melting point).

For example, the solid molecular dispersion of this invention may be prepared by a process comprising the steps of:

melting a mixture comprised of a solid lipid-based surfactant having an HLB (Hydrophile-Lipophile Balance) value greater than or equal to 10 and a solid stiffening agent having a melting point in the range of 50° C. to 80° C.;

dissolving a compound, specifically a sparingly water-soluble compound, in the melted surfactant and stiffening agent mixture to form a homogeneous liquid composition of the compound, surfactant and a stiffening agent;

and cooling the liquid composition.

In another embodiment, the solid molecular dispersion may be prepared by a process comprising the steps of:

melting a solid lipid-based surfactant having an HLB value greater than or equal to 10;

melting a solid stiffening agent having a melting point of from 50° C. to 80° C.;

dissolving a compound in the melted surfactant and mixing the melted stiffening agent with the compound-surfactant solution to form a homogeneous liquid composition;

or dissolving a compound in the melted stiffening agent and mixing the melted surfactant with the compound-stiffening agent solution to form a homogeneous liquid composition;

and cooling the liquid composition.

DETAILED DESCRIPTION OF THE INVENTION

The solid molecular dispersions of this invention are microparticulate solids at room temperature, and which have been prepared by dissolving a sparingly water-soluble compound in a melted particulatable lipid carrier to provide a homogeneous mixture, and cooling the resultant mixture so that it solidifies with the compound substantially uniformly, molecularly dispersed therein. One embodiment of this invention is directed to compositions comprising a molecular dispersion of a sparingly water-soluble compound in a particulatable lipid carrier comprising a solid lipid-based surfactant and a stiffening agent, useful for the oral delivery of sparingly water-soluble compounds. As used herein, a sparingly water-soluble compound is a compound having a solubility in water of less than 100 µg/mL at 25° C. Another embodiment of this invention relates to an improved process for the preparation of these solid dispersion compositions as spherical microparticulates or microspheres of a desired size range (50 µm-500 µm). Advantageously, the spherical solid dispersion compositions may be prepared using the process of this invention without affecting the integrity of the carrier or the compound.

Without being bound to any theory, it is presently understood that each of the lipid-based surfactant and the stiffening agent function as a solvent for dissolving the compound, function to facilitate the homogeneous dispersion of the compound in the mixture thereof, and function to maintain the solution state of the compound in the solid molecular dispersion. During dissolution of the solid molecular dispersion (e.g., after oral administration to a subject or after placing in a dissolution medium), the lipid-based surfactant functions as an emulsifying agent to enhance solubilization of the compound in the dissolution medium, e.g., gastric fluid and intestinal fluid both under fed and fasted state.

A compound, specifically a sparingly water-soluble compound, is present in the solid molecular dispersion composition of this invention in an amount of from about 0.01% to about 15% of the total weight of the dispersion, preferably, in the range of about 1% to about 10% of the total weight of the dispersion. In one embodiment of this invention, the sparingly water-soluble compound is present in the solid molecular dispersion in an amount of about 2% to about 5% of the total weight of the dispersion. Examples of sparingly water-soluble compounds are those that have a solubility in water of less than 100 µg/mL at 25° C. Such compounds have poor oral bioavailability and include lipophilic drugs, vitamins, and hormones. These compounds include steroids, steroid antagonists, non-steroidal anti-inflammatory agents, antifungal agents, antibacterial agents, antiviral agents, anticancer agents, anti-hypertensive agents, anti-oxidant agents, anti-epileptic agents, anti-depressant agents, and non-peptide enzyme inhibitors among many others. This invention also provides a way to increase the oral bioavailability of a sparingly water-soluble compound. More particularly, the invention relates to a water dispersible solid molecular dispersion of a sparingly water-soluble compound in a lipidic carrier comprised of a lipid-based surfactant and a stiffening agent.

The concentration of the lipid-based surfactant in the particulatable lipidic carrier of the solid molecular dispersions of this invention is in the range of about 5-50% of the total weight of the particulatable lipidic carrier, preferably in the range of about 10% to about 50% of the total weight of the particulatable lipidic carrier. The lipid-based surfactant is a water soluble or dispersible lipidic material, or mixture of lipidic materials, having a melting point in the range of 40° C.-50° C. and having an HLB value greater than 10. Without being bound to any theory, it is believed that one function of the lipid-based surfactant is to function as an emulsifying agent for the sparingly water-soluble compound upon precipitation in the dissolution media or in the gastrointestinal fluids. Thus, the rate of dissolution of the compound may be controlled by appropriate selection of the lipid-based surfactant and/or the concentration of the surfactant in the lipidic carrier. The lower the HLB value of the surfactant (about 10 to about 5), the more hydrophobic it is. Conversely, the higher the HLB value of the surfactant (about 13 to about 18), the more hydrophilic it is. Accordingly, a solid molecular dispersion containing a sparingly water-soluble compound and a lipid-based surfactant having a high HLB value will provide a dispersion that has a compound release rate that is faster than the dispersion containing a lipid-based surfactant having a low HLB value. A solid molecular dispersion containing a sparingly water-soluble compound and a high concentration (40-50% w/w) of a lipid-based surfactant will provide a dispersion that has a compound release rate that is faster than the dispersion containing a low concentration (5-15% w/w) of the surfactant. Based on the disclosure herein and routine experimentation, those skilled in the art will understand how to balance surfactant selection and surfactant concentration to obtain a solid molecular dispersion with a desired compound release rate.

After oral administration of a solid molecular dispersion of this invention and exposure to body fluids, such as gastric fluid and intestinal fluids, the dispersion can emulsify (self-emulsifying drug delivery systems or (SEDDS)) to form fine colloidal micelle dispersions of the sparingly water soluble compound and the lipid-based surfactant and/or stiffening agent in the gastrointestinal milieu. Advantageously, the carrier in the solid molecular dispersion of this invention is a lipidic carrier. Lipid-based compositions have been shown to increase the secretion of endogenous bile salts (BS) and biliary lipids (BL), including phospholipids (PL) and cholesterol (CH), which lead to the formation of intestinal micelles, which in turn, can increase the solubilization capacity of the intestinal fluid. These intestinal micelles may interact with the compound-containing micelles to further protect the compound from interactions with food and/or digestive enzymes that may be present in the gastrointestinal milieu. Because these intestinal micelles are present in close proximity to the absorption sites in the intestine, interaction of the intestinal micelles with the compound-containing micelles may lead to enhanced solubilization and absorption resulting in elevated plasma concentration of the compound.

Accordingly, the lipid-based surfactant present in the solid molecular dispersion of this invention may be used to control the release of the sparingly water-soluble compound by modulating the hydrophilicity or hydrophobicity of the dispersion and may be used as an emulsifying agent for the compound by forming colloidal dispersions (SEDDS) in an aqueous environment. The emulsification of the compound/drug would result in enhanced solubilization in the GI milieu both under fed and fasted state conditions with concomitant increase in absorption and bioavailability of the compound/drug.

The concentration of the stiffening agent (mixed glycerides) in the particulatable lipidic carrier of the solid molecular dispersions of this invention is in the range of about 50% to about 95% of the total weight of the particulatable lipidic carrier, preferably in the range of about 50-75% of the total weight of the particulatable lipidic carrier.

Suitable lipid-based surfactants and stiffening agents are those in which the sparingly water-soluble compound is soluble and which possess a melting point >40° C.

Examples of suitable polyglycolized glycerides useful as a lipid-based surfactant in the solid dispersions of this invention include lauroyl macrogoglycerides and stearoyl macrogoglycerides (Gelucire® 44/14 and Gelucire® 50/13 respectively, sold by Gattefosse Corporation, West Kindermack Road, N.J.). These surfactants disperse in an aqueous media forming micelles, microscopic vesicles or globules. Lauroyl macrogoglycerides and stearoyl macrogoglycerides are digestible GRAS materials that are available as a semi-solid waxy material or granules or pastilles with HLB values of about 14 and 13 and melting points of about 44° C. and 50° C., respectively.

Examples of suitable polyoxyethylene castor oil derivatives useful as a lipid surfactant in the solid dispersions of this invention include polyoxyl 60 hydrogenated castor oil (sold by BASF Corporation, Mount Olive, N.J. under the tradename Cremophor. RH60®). Cremophor RH60® is available as a white, semi-solid paste with a faint characteristic odor and is almost tasteless. This surfactant has an HLB value of about 15-17 and a melting point of about 40° C.

Examples of suitable polyoxyethylene stearates useful as surfactants in the solid dispersions of this invention include polyoxyethylene 50 stearate (sold under the tradename Myrj®53, by Uniqema (a division of ICI), New Castle, Del.). These surfactants are typically available as creamy-colored waxy solids, have HLB values of greater than 15 and melting points of about 42° C.-52° C.

The stiffening agent in this invention is comprised of mixed glycerides comprised of long chain fatty acid esters. Advantageously, the stiffening agent has an overall melting point in the range of 50° C.-80° C. and has the ability to solidify rapidly from a molten state. The mixed glycerides used herein as a stiffening agent may also solubilize the sparingly water soluble compound and inhibit the compound's molecular mobility in the dispersion matrix, thus improving the physical and chemical stability of the compound during storage.

The glycerides used as stiffening agents in the solid molecular dispersion of this invention are long chain fatty acid esters. Without being bound to any theory, it is believed that the stiffening agent functions to enable particle formation during processing, functions as a solubilizer for the sparingly water soluble compound and functions to prevent compound recrystallization (crystallization inhibitor) by inhibiting molecular mobility of the compound in the dispersion, thereby improving the physical and chemical stability of the solid molecular dispersion during storage. The glycerides used herein are derived from edible oils and fats obtained from suitable fatty acid sources such as cotton seed oil, palm oil, lard, tallow, etc. Examples of suitable stearates useful as a stiffening agent in the solid dispersions of this invention include glycerol monostearate (GMS) sold under the tradenames Myverol 18-07® and Imwitor 491®. Myverol 18-07® is food grade glycerol monostearate, sold by Quest International, Hoffman Estates, Ill. Imwitor 491® is pharmaceutical grade glycerol monostearate sold by Sassol, Germany. Both of these products are available as small, free flowing microbeads which have an average molecular weight of about 350 and melting points in the range of 50° C.-70° C. Another example of a suitable stearate useful as a stiffening agent in the solid dispersions of this invention is the glycerol palmitostearate sold under the tradename Precirol ATO5®, sold by Gattefosse Corporation, West Kindermack Road, N.J. Precirol ATO5® is available as a fine white powder having a melting point in the range of 52° C.-55° C. Further examples of suitable stearates useful as a stiffening agent in the solid dispersions of this invention include the hydrogenated vegetable oil (mixed glycerides) Sterotex®HM, Sterotex®K, Sterotex®NF which are commercially available from Abitec Corporation, Janeswille, Wis. These hydrogenated vegetable oils are available as fine powder, flakes or pellets, with melting points in the range of 60° C.-70° C.

The solid molecular dispersion formulations of this invention may further comprise one or more conventional formulation co-agents, such as one or more disintegrating agents, one or more flow agents, one or more solubilization enhancers, one or more pore-forming agents, or a mixture thereof. Generally, the total weight of the one or more formulation co-agents in the solid molecular dispersion is about 0.01% to about 5% by weight of the solid dispersion.

Exemplary disintegrating agents that are suitable for use in this invention include crospovidone (sold by BASF Corporation, Mount Olive, N.J. under the tradename Polyplasdone™), sodium starch glycolate (sold by Generichem Corporation, Totowa, N.J., under the tradename Explotab™), croscarmellose sodium (sold by FMC Corporation, Philadelphia, Pa. under the tradename Aci-Di-Sol™) and a mixture thereof.

Exemplary suitable flow agents include silicon dioxide, amorphous fumed silica, starch, synthetic amorphous fumed silica, precipitated silica, and colloidal silica (sold by Cabot Corp., Tuscola, Ill. under the trade name Cab-O-Sil®) and a mixture thereof.

Exemplary pore-forming agents suitable for use in this invention include sucrose, sodium chloride, potassium chloride, dextrose, mannitol and a mixture thereof.

When the solid molecular dispersion is formulated into a tablet or pill, the tablet or pill may be further coated or otherwise compounded with pharmaceutically acceptable materials known in the art to provide a dosage form affording prolonged action or delayed or sustained release.

Most powdered materials can be kept free flowing by adding a suitable flow agent at a concentration of about 0.5% to about 2% of total weight of the solid molecular dispersion. Preferably, the weight percent of the flow agent in the final product will be in the range of about 1-2% (total weight).

Advantageously, at least one solubilization enhancer or dispersion agent may be added to the compound/lipidic carrier mixture to enhance the solubility, flow and/or dissolution, of the compound in the lipidic carrier.

Exemplary solubilization enhancers that are suitable for use in this invention include mid-weight polyethylene glycol having a molecular weight of from 2000 to 8000. Preferably, the solubilization enhancer is a polyethylene glycol with an average molecular weight ranging from 2000 to 6000, more preferably from 3000 to 6000. Particularly preferred PEG's useful in the solid dispersions of the present invention are PEG 3350 (also referred to as Carbowax™Sentry™Polyethylene Glycol 3350 Powder NF), and PEG 6000, available from Union Carbide Corporation, Danbury, Conn.

Advantageously, the composition of the solid molecular dispersions of this invention may be modified so as to vary the solubilization rate of the sparingly water-soluble compound by varying the type and relative concentration of the lipid-based surfactant and stiffening agent in the carrier matrix. For example, solid dispersion compositions containing a unit dose of a compound (solubility in water of about 5 µg/mL) in a water-dispersible lipidic carrier composed of glycerol monostearate (GMS) and Gelucire®50/13 at two different weight ratios, 50:50 and 90:5, respectively, showed differences in the rate of solubilization of the compound in a dissolution medium (2.0% w/v of sodium lauryl sulfate) kept under sink conditions, FIG. 1. Increasing the amount of the lipid-based surfactant (i.e., increasing the hydrophilicity of the dispersion matrix) resulted in. faster solubilization of the compound. Such variations and modifications may be made by one of ordinary skill in the art with routine experimentation.

In addition, a sparingly water-soluble compound formulated in the solid molecular dispersions of this invention may be 2 to 10 times more soluble than the unformulated compound, when evaluated after one hour of dissolution in standard USP-II Dissolution Apparatus under non-sink conditions (i.e., non-sink refers to the solubility limit of the compound in the media, typical sink conditions described by the USP comprise dissolving a compound in a solvent, wherein the concentration of the compound is one-fifth to one-third the limit of solubility concentration of the compound in the selected solvent).

A further advantage of the solid molecular dispersions of this invention is that the composition of the carrier matrix and the process for the preparation of the dispersion provide flexibility in the selection of the final physical form of the dispersion. Without being bound to any theory, it is believed that such flexibility is obtained because the lipid-based surfactants and stiffening agents useful in the molecular dispersions of this invention have relatively low meting points, the sparingly water-soluble compound remains dissolved in the carrier even upon cooling and the use of a stiffening agent in the carrier matrix that can crystallize or congeal rapidly from a molten state to form particles. Advantageously, the liquid composition, formed on dissolving a sparingly water-soluble compound in the lipid-based surfactant and stiffening agent, may be processed into water-dispersible microparticulates in single step process that can overcome disadvantages of conventional production technology for solid dispersions.

Current methods for producing solid dispersion microparticulates on a commercial scale use melt extrusion or spray congealing process. In a melt extrusion process, a compound is co-extruded with a carrier which forms a solid solution upon cooling and solidifying. The extrudates are then milled and sieved to produce particles of a desired size range to ensure good dissolution. This method suffers from many disadvantages, including: compound loading, down stream product handling (for e.g., pulverization of solid dispersion extrudates into particles is often difficult because carriers are tacky), lengthy cleaning time and, high capital investment. In a spray congealing process the compound is dispersed in the molten carrier and atomized using a spray nozzle into a cooling chamber or tower into which cold air is circulated. The atomized droplets congeal or solidify on coming into contact with air. Though this process produces particles from a liquid feed in a single step, the method suffers from one major disadvantage, that is, the feed to spray nozzle must be at least 20-30° C. above the temperature at which solidification commences to avoid blockage problems in feed pipes and in the atomizer nozzle. Blockage in the feed tubes and/or spray nozzle will result in lengthy cleaning times. In addition, the spray chamber has to be maintained at a lower temperature (10° C.-15° C.) to cause solidification of the atomized droplets into particles. The particles produced using this process are polydisperse which may result in variability in the dissolution rates.

The method used in this invention comprises employing a rotating disk atomization process for producing microparticulates from a molten liquid feed in a single step that can overcome limitations of the current production methods. The process is simple and robust in terms of producing particles of a desired size distribution (50 µm-500 µm) with a high compound loading and provides operating versatility from a standpoint of handling different types of carrier materials. The process is capable of producing particles at a rate up to 500 lb/hr (dry basis). Rotating disk atomization process is currently used for commercial manufacturing of microspheres containing microorganisms, vitamins, antiperspirants, deodorants, solvents, etc., using fatty acids, polyethylene waxes, and other low melting point materials (including low molecular weight polymers).

A description of such rotary disk processing for encapsulation of non-pharmaceutical materials is provided in U.S. Pat. No. 5,292,657 and, No. 5,601,761 and the references cited therein. Rotary disk processing also provides for the capability of preparing coated microsphere particles. U.S. Pat. Nos. 4,675,140 and, No. 4,386,895 and the references cited therein, provide a description of one way to use rotary disk processing to obtain coated particles. The liquid composition may also be processed using extruders, which can provide coated or uncoated dosage forms ranging in size from microspheres to tablets, as described in U.S. Pat. No. 4,957,681, No. 4,880,585, No.6,316,473, and the references cited therein.

The method used in the present invention for producing solid dispersion microparticulates or microspheres having a melting point above the ambient temperature comprises of the following steps. The first step comprises forming a molten lipidic carrier by melting, the lipid-based surfactant and stiffening agent by heating to a temperature that is about 10° C.-20° C. above the melting point of the highest melting material, and dispersing or dissolving the compound into the molten carrier by continuous stirring under a nitrogen blanket. The concentration of the compound in the lipidic carrier may range from 0.5-15% w/w. Preferably the concentration is in the range of 5-10%, based on the total weight of the compound and the lipidic carrier. The viscosity of the compound/carrier blend may range from 1-20 poise, more preferably from 5-10 poise. The compound is dispersed or dissolved into the lipidic carrier melt using a high-speed mixer. The temperature of feed solution is in the range of 70° C.-100° C. In the second step, the compound/carrier blend is fed at a controlled rate using a gravity feeding mechanism to the center of a rotating disk. Preferably, the feed temperature is in the range of 80° C.-90° C. The process use a 4-inch rotary disk that can run from 2,000-20,000 RPM. The preferred disk speed will range from 6,000-7,000 RPM. The feed rate is in the range of 0.5-1.0 grams/second, more preferably from 0.25-0.75 grams/second. The disk is kept at a temperature above the melting temperature of the carriers to ensure that the carriers are in a liquid state on the surface of the disk. The disk surface is heated using an induction heating mechanism. The disk temperature can range from 70° C.-130° C., more preferably from 90° C.-120° C. Due to the rotation of the disk a thin film is formed on the surface the disk. In the third step, the liquid film is thrown radially outward from the surface of the disk as droplets which solidify or congeal upon contact with the surrounding carrier gas (air or nitrogen or argon). The processing can be done under a inert environment (nitrogen or argon purge) to prevent degradation of the lipidic carrier and the compound at elevated temperatures. The speed of rotation affects the size of the microspheres that are produced in this process. That is, with other factors remaining constant, increased rotational speed results in production of smaller microspheres at a faster rate while decreased rotational speed results in production of larger particles at a slower rate. The desired particle size of the microparticulates produced is in the range of 50 μm-500 μm. The microparticulates or microspheres produced preferably has a melting point between 40° C.-55° C.

The solid dispersions of this invention are spherical microparticulates that form free flowing powders that can be blended easily with other excipients or compounds that may be filling into capsules or compressed into tablets that can be coated with polymers to modulate compound release and targeting.

The preparation of solid molecular dispersions of a compound, specifically a sparingly water-soluble compound, of this invention may be prepared by the methods described in the following non-limiting examples.

EXAMPLE 1

Solid molecular dispersion formulations #1 and #2 containing of two different grades of Gelucires® (44/14 and 50/13, respectively, ) were prepared to demonstrate the effect of HLB value and melting point on the rate of dissolution of Test Compound I (having a water solubility of <5 μg/mL). The composition of the lipid carrier for the two solid dispersions is summarized in the Table below.

| Components | Composition Expressed in % w/w | |
|---|---|---|
| | # 1 | # 2 |
| Test Compound I | 10.0 | 10.0 |
| GMS | 45.0 | 45.0 |
| Gelucire ® 44/14 | 45.0 | — |
| Gelucire ® 50/13 | — | 45.0 |

Note:
GMS—Glycerol Monostearate (stiffening agent)

The required quantities of the lipidic carrier components, Glycerol Monostearate (GMS) and Gelucire® 44/14 or Gelucire® 50/13, were heated to about 75° C.-80° C. in a container under an inert atmosphere (nitrogen blanket) until the components melted and formed a clear, homogeneous mixture. A high speed mixer ensured proper mixing of the carrier components. The compound was dissolved into the molten carrier with continuous stirring. The lipidic carrier melt containing the dissolved compound was subsequently atomized into droplets using a rotating disk, wherein the compound/carrier melt was congealed into particles upon contact with a carrier gas (e.g., argon) in the disk chamber. The disk speed was 7,000 RPM and the disk temperature was maintained at 80° C. using an induction heater. The feed rate to the disk was 0.5 g/sec. The disk chamber was kept under argon purge during the disk run and the particles were collected from the bottom of the chamber.

Figure 2:
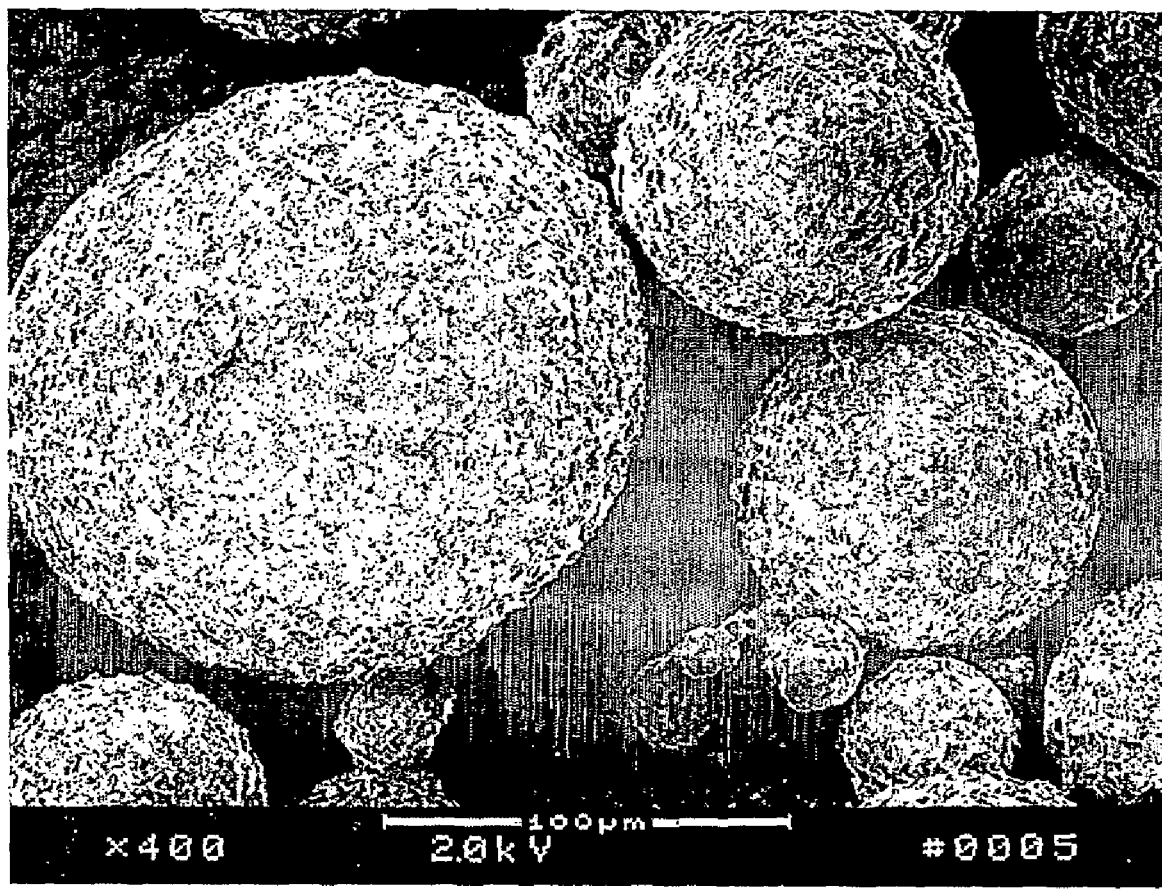
FIGS. 2 and 3 are scanning electron micrographs of microparticulates prepared by the process of this invention.
Figure 3:
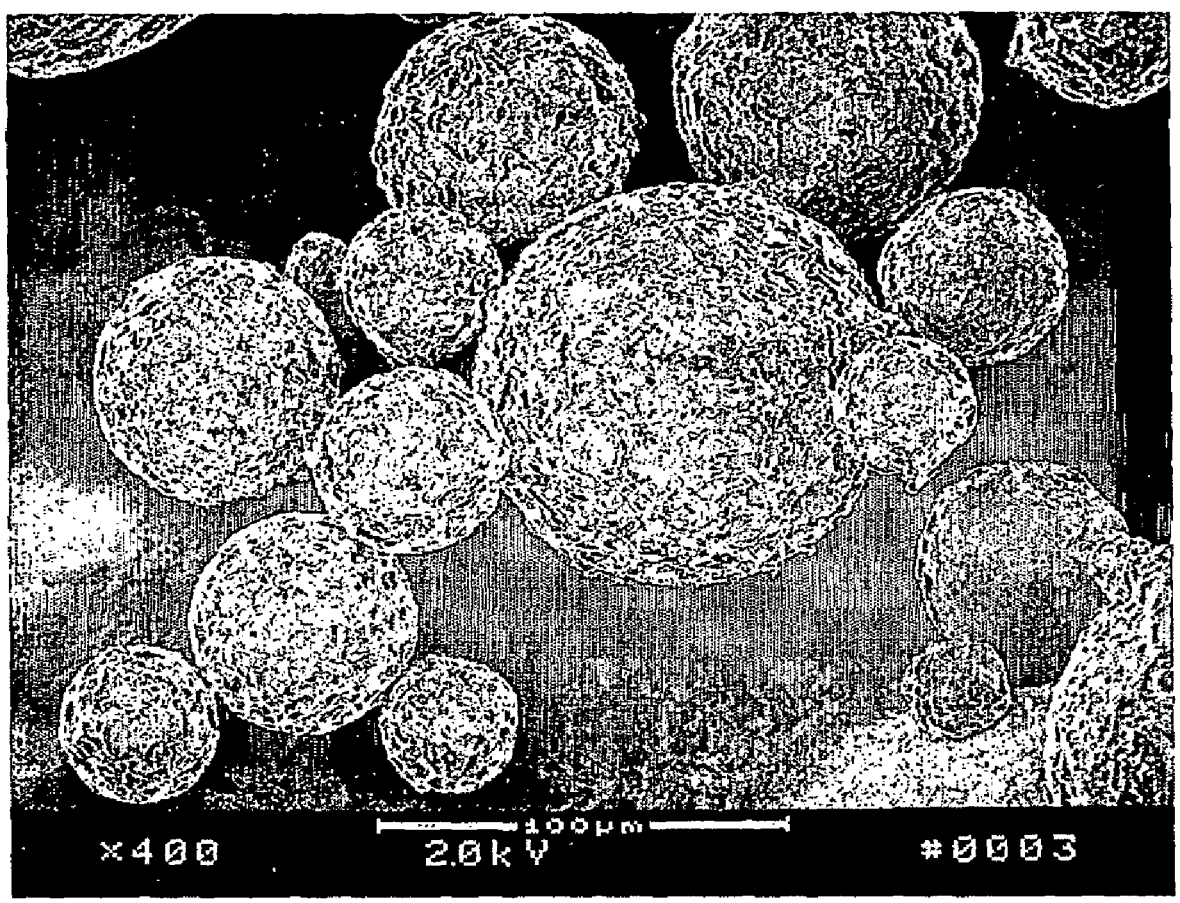

The SEM micrographs of microparticulates or microspheres prepared for the two lipid-based compositions are shown in FIGS. 2 and 3. The particles were spherical with majority of the particle in the range of 50 μm-150 μm. Dissolution studies were done on the microparticulates in physiologically relevant media, simulated gastric fluid (0.1N HCl, pH 1.2, no enzymes added) and simulated intestinal fluid (fed state, pH 5.0), in terms of pH conditions and composition encountered in gastrointestinal tract to better predict compound dissolution in-vivo.

Figure 4:
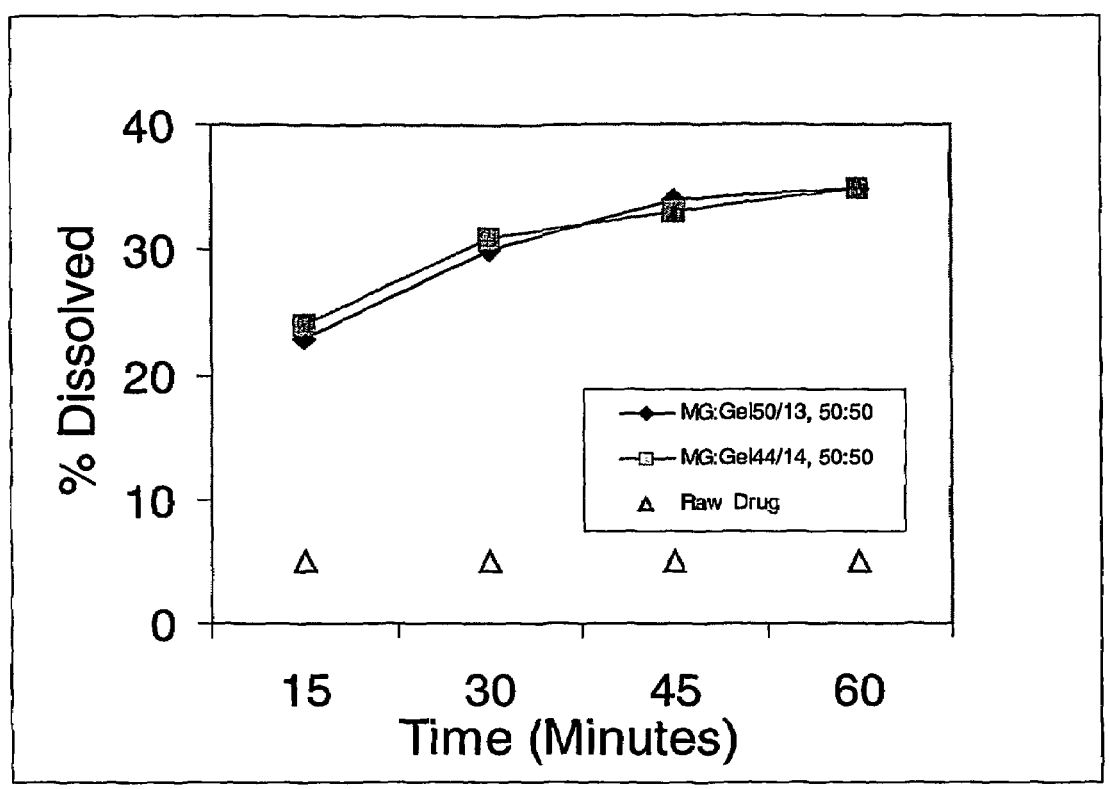
FIGS. 4 and 5 illustrate the rate of dissolution of a compound, alone, and as formulated in two water-dispersible lipidic carriers, composed of glycerol monostearate and Gelucire®50/13 and glycerol monostearate and Gelucire®44/14 each at 50:50 weight ratios
Figure 5:
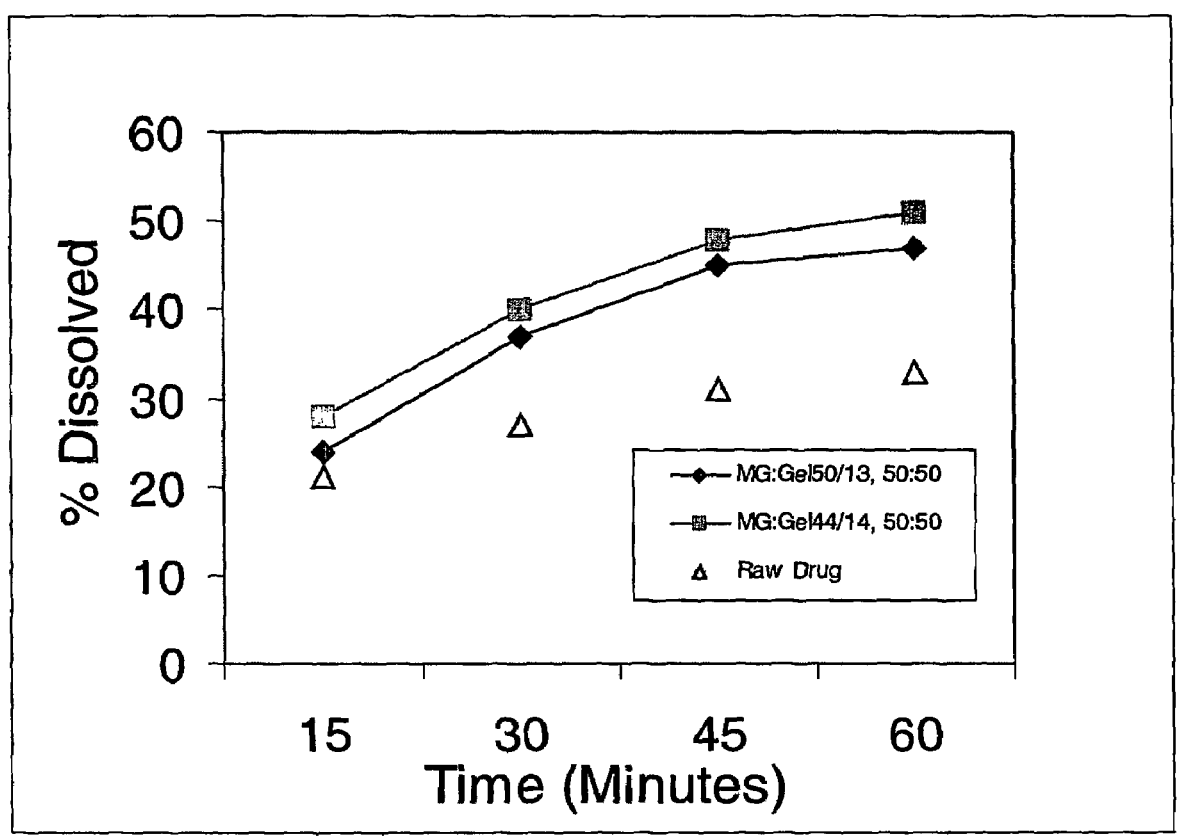

In these studies a unit dose (raw test compound or formulation containing 10 mg of Test Compound I) was filled into size 0 gelatin capsules and placed in a Teflon coated sinker. A sinker containing the capsule was drooped into the dissolution medium (volume—500 mL) that was maintained at 37° C. Gentle agitation was provided by a paddle rotating at 75 RPM. Samples were taken at predetermined time points and analyzed by UV absorbance to determine the rate and extent of solubilization of the compound. The solubilization rate for the unformulated compound and the solid dispersion compositions in the two dissolution mediums are shown in FIGS. 4 and 5. The rate and extent of solubuilization of Test Compound I was higher for the solid dispersion microparticulate as compared to the unformulated compound, FIGS. 4 and 5. Also, the rate of solubilization of Test Compound I was faster for solid dispersion composition that incorporated a surfactant with a higher HLB and lower melting point (i.e., Gelucire®44/14).

EXAMPLE 2

Solid dispersion particulates that incorporated a flow agent was prepared using the spinning disk process as described in Example 1. The composition of the lipid carrier in the solid dispersion is summarized in the Table below.

| Components | Composition Expressed in % w/w |
|---|---|
| Test Compound I | 10.0 |
| GMS | 50.0 |
| Gelucire ® 50/13 | 50.0 |
| Sylloid ® | 2.0 |

Figure 6:
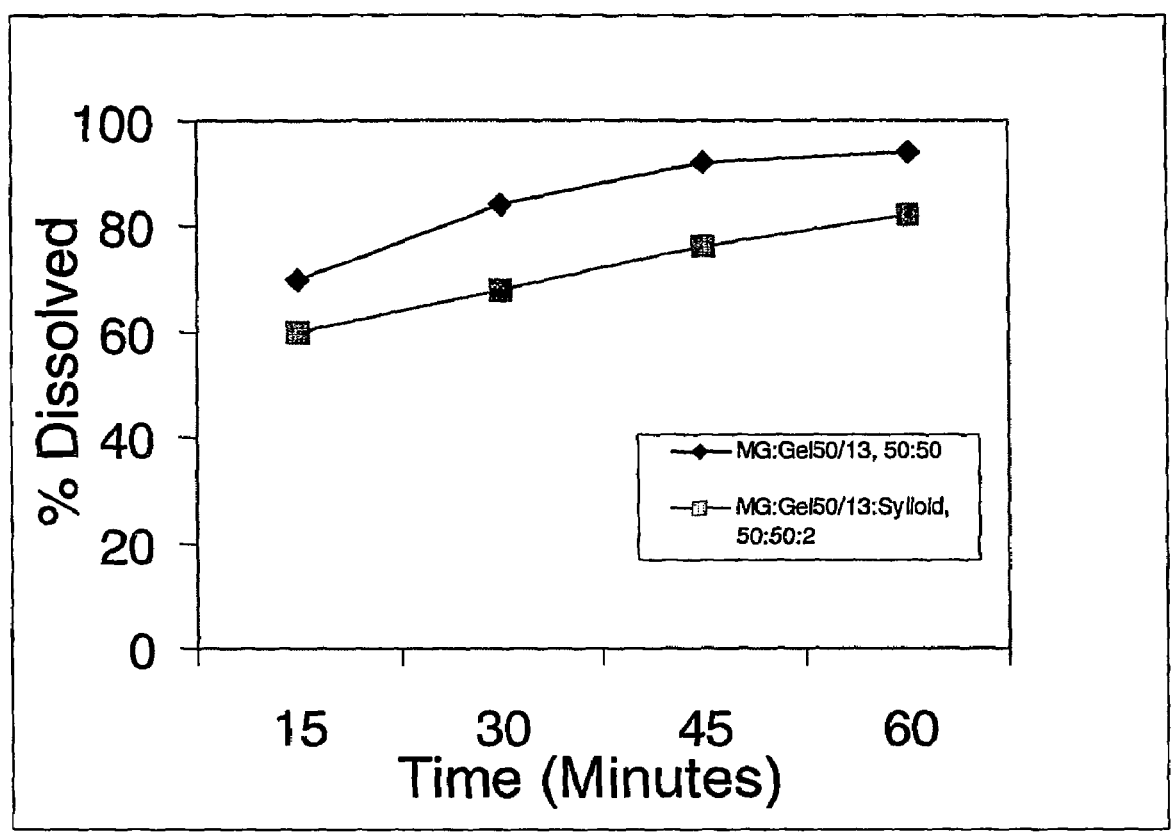
FIG. 6 illustrates the rate of dissolution of solid molecular dispersions composed of glycerol monostearate and Gelucire®50/13 (50:50), with and without a flow agent.

The particles prepared had excellent flow properties. Dissolution studies were conducted on these particles in a dissolution medium kept under sink conditions (2.0% w/v of sodium lauryl sulfate) as described in Example 1. The solubilization rate for this solid molecular dispersion compared to a control molecular dispersion formulation (no flow agent) is shown in FIG. 6.

All publications, including, but not limited to, patents and patent applications cited in this specification, are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration it is believed that one skilled in the art can, given the preceding description, utilize this invention to its fullest extent. Therefore any examples are to be construed as merely illustrative and not a limitation on the scope of this invention in any way. The embodiments of the invention in which an exclusive property or privilege is claimed are defined as follows.

What is claimed is:

1. A water-dispersible particulate composition having an overall melting point of 40° C. or higher which is a solid molecular dispersion comprised of:
   about 0.01% to about 15% by weight of a sparingly water-soluble compound and about 85-99.99% by weight of a particulatable lipid-based carrier,
   wherein the particulatable lipid-based carrier is comprised of:
   about 5% to about 50% by weight of a lipid-based surfactant selected from the group consisting of a polyglycolized glyceride, a polyoxyethylene castor oil derivative, a polyoxyethylene stearate having a melting point of from 40° C. to 50° C., and a mixture thereof, and
   about 50% to about 95% by weight of a stiffening agent having a melting point of from 50° C. to 80° C. and selected from the group consisting of glycerol monostearate, glycerol palmitostearate, hydrogenated vegetable oil, and a mixture thereof.

2. The water-dispersible particulate composition of claim 1 prepared by a process comprising the steps of:
   melting a mixture comprised of the lipid-based surfactant and the stiffening agent, wherein the lipid-based surfactant is a solid lipid-based surfactant having an HLB value greater than or equal to 10;
   dissolving the compound in the melted surfactant and stiffening agent mixture to form a homogeneous liquid composition of the compound, surfactant and stiffening agent;
   and cooling the liquid composition.

3. The water-dispersible particulate composition according to claim 1 prepared by a process comprising the steps of:
   melting the lipid-based surfactant, wherein the lipid-based surfactant is a solid lipid-based surfactant having an HLB value greater than or equal to 10;
   melting the stiffening agent having a melting point of from 50° C. to 80° C.;
   dissolving the compound in the melted surfactant;
   mixing the stiffening agent with the dissolved compound-surfactant mixture to form a homogeneous liquid composition; and
   cooling the liquid composition.

4. The water-dispersible particulate composition according to claim 1, wherein the compound is present in the composition in an amount of from about 1% to about 10%.

5. The water-dispersible particulate composition according to claim 1, wherein the compound is present in the composition in an amount of from about 2% to about 5%.

6. The water-dispersible particulate composition according to claim 1, wherein the lipid-based surfactant is present in an amount of from about 10% to about 50% by weight of the lipid-based carrier.

7. The water-dispersible particulate composition according to claim 1, wherein the stiffening agent is present in an amount of from about 50% to about 75% by weight of the lipid-based carrier.

8. The water-dispersible particulate composition according to claim 1, further comprising one or more formulation co-agents selected from the group consisting of a disintegrating agent, a flow agent, a solubilization enhancer and a pore-forming agent.

9. The water-dispersible particulate composition according to claim 8, wherein the total weight of the one or more formulation co-agents in the composition is 0.01% to 5% by weight of the composition.

10. The water-dispersible particulate composition according to claim 8, wherein the disintegrating agent is selected from the group consisting of crospovidone, sodium starch glycolate, croscarmellose sodium and a mixture thereof.

11. The water-dispersible particulate composition according to claim 8, wherein the flow agent is selected from the group consisting of colloidal silicon dioxide, amorphous fumed silica, starch, synthetic amorphous fumed silica, precipitated silica, and fumed silica and a mixture thereof.

12. The water-dispersible particulate composition according to claim 8, wherein the solubilization enhancer is selected from the group consisting of mid-weight polyethylene glycol having a molecular weight of from 2000 to 8000, and a mixture thereof.

13. The water-dispersible particulate composition according to claim 8, wherein the pore-forming agent is selected from the group consisting of sucrose, sodium chloride, potassium chloride, dextrose and a mixture thereof.

14. A process for preparing the water-dispersible particulate composition according to claim 1, comprising the steps of:
   melting a mixture comprised of the lipid-based surfactant and the stiffening agent, wherein the lipid-based surfactant is a solid lipid-based surfactant having an HLB value greater than or equal to 10;
   dissolving the compound in the melted surfactant and stiffening agent mixture to form a homogeneous liquid composition of the compound, surfactant and stiffening agent;
   and cooling the liquid composition.

15. A process for preparing the water-dispersible particulate composition according to claim 1, comprising the steps of:

melting the lipid-based surfactant, wherein the lipid-based surfactant is a solid lipid-based surfactant having an HLB value greater than or equal to 10;

melting the stiffening agent having a melting point of from 50° C. to 80° C.;

dissolving the compound in the melted surfactant;

mixing the stiffening agent with the dissolved compound-surfactant mixture to form a homogeneous liquid composition; and cooling the liquid composition.

16. A process according to claim 14, further comprising cooling the liquid composition using rotary disk processing.

17. A process according to claim 16, comprising cooling the liquid composition using rotary disk processing to produce microspheres with a median particle size in the range of 50 μm-500 μm.

18. A process according to claim 15, further comprising cooling the liquid composition using rotary disk processing.

19. A process according to claim 18, comprising cooling the liquid composition using rotary disk processing to produce microspheres with a median particle size in the range of 50 μm-500 μm.

* * * * *